(12) United States Patent
Wells

(10) Patent No.: US 9,767,694 B1
(45) Date of Patent: Sep. 19, 2017

(54) INTOXICATED PEDESTRIAN DETECTION SYSTEM

(71) Applicant: DENSO International America, Inc., Southfield, MI (US)

(72) Inventor: Bryan Wells, Oceanside, CA (US)

(73) Assignee: Denso International America, Inc., Southfield, MI (US)

( * ) Notice: Subject to any disclaimer, the term of this patent is extended or adjusted under 35 U.S.C. 154(b) by 0 days.

(21) Appl. No.: 15/251,103

(22) Filed: Aug. 30, 2016

(51) Int. Cl.
*G08G 1/00* (2006.01)
*G08G 1/16* (2006.01)
*G08G 1/0962* (2006.01)

(52) U.S. Cl.
CPC ........... *G08G 1/166* (2013.01); *G08G 1/0962* (2013.01)

(58) Field of Classification Search
CPC .............................. G08B 1/166; G08G 1/0962
USPC .......... 340/506, 539.1, 539.11, 425.5, 426.1, 340/539.13, 573.1
See application file for complete search history.

(56) References Cited

U.S. PATENT DOCUMENTS

2015/0091740 A1* 4/2015 Bai .................. G08B 21/06 340/901

\* cited by examiner

*Primary Examiner* — Daryl Pope
(74) *Attorney, Agent, or Firm* — Harness, Dickey & Pierce, P.L.C.

(57) ABSTRACT

Devices, systems, and methods for detecting whether a pedestrian is intoxicated. When it is determined that the pedestrian is intoxicated, a notification is transmitted to nearby drivers and others. The drivers can then take action to avoid the pedestrian and assist the pedestrian as appropriate.

20 Claims, 2 Drawing Sheets

INTOXICATED PEDESTRIAN DETECTION SYSTEM

FIELD

The present disclosure relates to devices, systems, and methods for detecting intoxicated pedestrians, and informing others that an intoxicated pedestrian is nearby.

BACKGROUND

This section provides background information related to the present disclosure, which is not necessarily prior art.

Informing vehicle drivers that they are approaching a pedestrian who is intoxicated could help reduce, or eliminate, accidents with intoxicated pedestrians. The present teachings thus advantageously provide for devices, systems, and methods for detecting intoxicated pedestrians, and informing drivers and others that an intoxicated pedestrian is nearby. The drivers can then take action to avoid the pedestrian and assist the pedestrian as appropriate.

SUMMARY

This section provides a general summary of the disclosure, and is not a comprehensive disclosure of its full scope or all of its features.

The present teachings advantageously provide for devices, systems, and methods for detecting whether a pedestrian is intoxicated. When it is determined that the pedestrian is intoxicated, a notification is transmitted to nearby drivers and others. The drivers can then take action to avoid the pedestrian and assist the pedestrian as appropriate.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of select embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
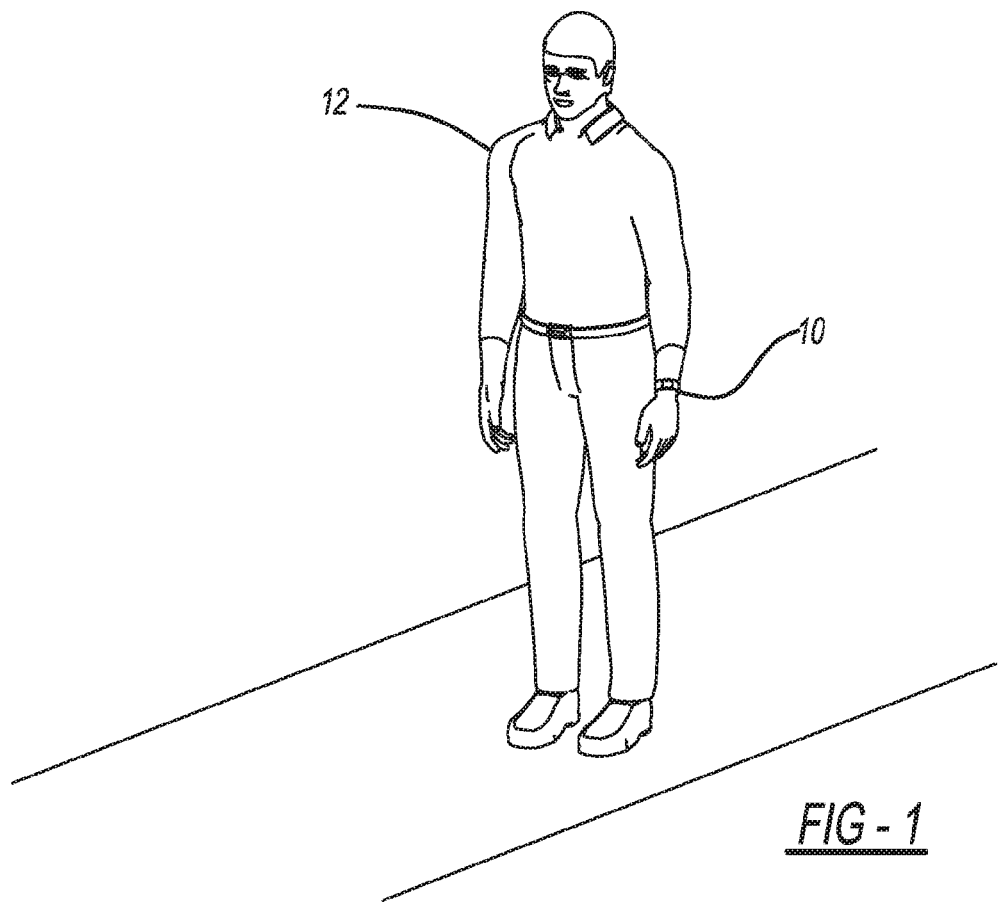
FIG. 1 illustrates an exemplary device according to the present teachings for detecting an intoxicated pedestrian.

With initial reference to FIG. 1, a device configured to detect whether a person is intoxicated is generally illustrated at reference numeral 10. Although the device 10 is illustrated as a wearable device in the form of a bracelet or watch, the device 10 can be any suitable device configured to detect whether a person is intoxicated. For example, the device 10 can be a mobile telephone, such as a smartphone, or any suitable monitoring device configured to sense and monitor movement and/or physical conditions of the user/wearer. The device 10 can be used/worn by any suitable individual, such as a pedestrian 12.

Figure 2:
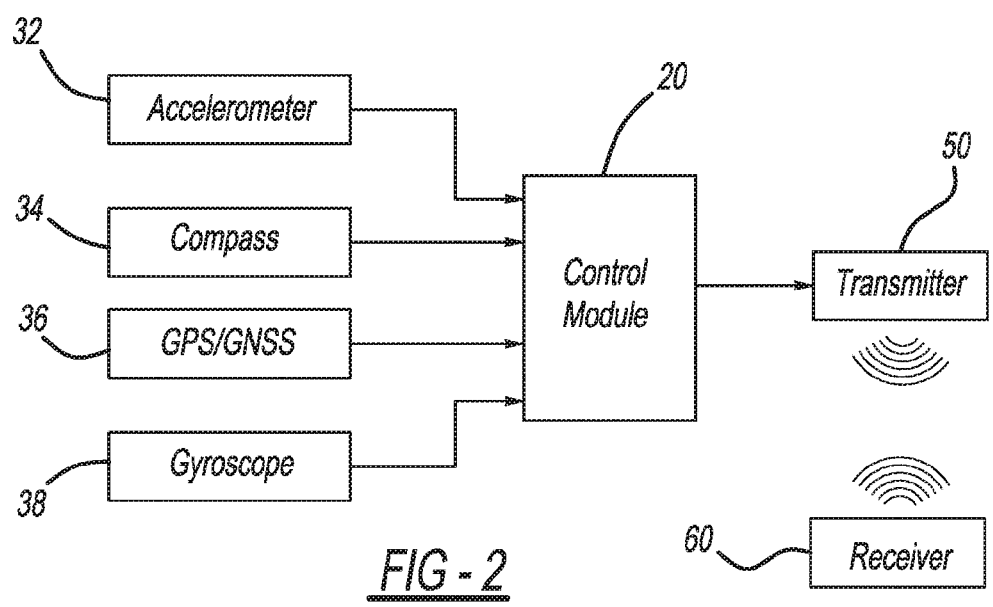
FIG. 2 illustrates components of the device of FIG. 1.

FIG. 2 illustrates exemplary features of the device 10. For example, the device 10 includes a control module 20. In this application, the term "module" or the term "controller" may be replaced with the term "circuit." The term "module" may refer to, be part of, or include processor hardware (shared, dedicated, or group) that executes code, and memory hardware (shared, dedicated, or group) that stores code executed by the processor hardware. The code is configured to provide the features of the modules, controllers, and systems described herein.

The control module 20 is configured to receive inputs from any suitable sensors, monitors, trackers, etc. configured to monitor physical conditions and/or movement of the pedestrian 12 that can identify whether or not the pedestrian 12 is intoxicated. For example, the control module 20 is configured to receive inputs from any suitable movement detectors, including an accelerometer 32, a compass 34, a global positioning system (GPS) or global navigation satellite system (GNSS), and/or a gyroscope 38.

The accelerometer 32 can be any suitable accelerometer configured to measure acceleration of the pedestrian 12. The compass 34 is configured to identify the direction that the pedestrian 12 is facing. The GPS/GNSS system 36 is configured to receive signals from orbiting satellites, or any other suitable source, and determine the location of the pedestrian 12 based on the signals. The gyroscope 38 is configured to identify and monitor orientation of the pedestrian 12.

Based on inputs from the movement detectors 32, 34, 36, and 38, the control module 20 is configured to compare movement of the pedestrian 12 with one or more stored movement patterns. Specifically, the control module 20 is configured to compare movement of the pedestrian 12 as sensed by movement detectors 32, 34, 36, 38 with stored movements of the pedestrian 12 when the pedestrian 12 was intoxicated (or with a stored profile of a generic intoxicated individual) to determine whether the pedestrian 12 is currently intoxicated. For example, if inputs from the movement detectors 32, 34, 36, 38 indicate that the pedestrian 12 is not walking linearly in a straight line and/or stumbling as compared to the normal walking patter of the pedestrian 12, then the control module 20 makes a determination that the pedestrian 12 is intoxicated. Operation of the movement detectors 32, 34, 36, and 38 will be further described herein in conjunction with the description of the method 110 of FIG. 3.

The control module 20 is further configured to, based on the inputs thereto from the movement detectors 32, 34, 36, and 38, operate a transmitter 50 to transmit a notification that the pedestrian 12 is intoxicated. The transmitter 50 can be configured to transmit the notification as any suitable signal, such as any suitable radio frequency signal. For example, the transmitter 50 can be configured as a dedicated short range communications (DSRC) transmitter. The transmitter 50 can be configured to transmit the notification using Wi-Fi, cellular transmission (e.g., LTE), or any other suitable wireless communications standard.

The transmitter 50 is configured to transmit the notification to any suitable receiver, such as a receiver 60. The receiver 60 can be incorporated into a vehicle, including any suitable motorized vehicle or non-motorized vehicle, such as a bicycle. The receiver 60 can also be included with any suitable portable electronic device, such as a smartphone or wearable electronic device.

Figure 3:
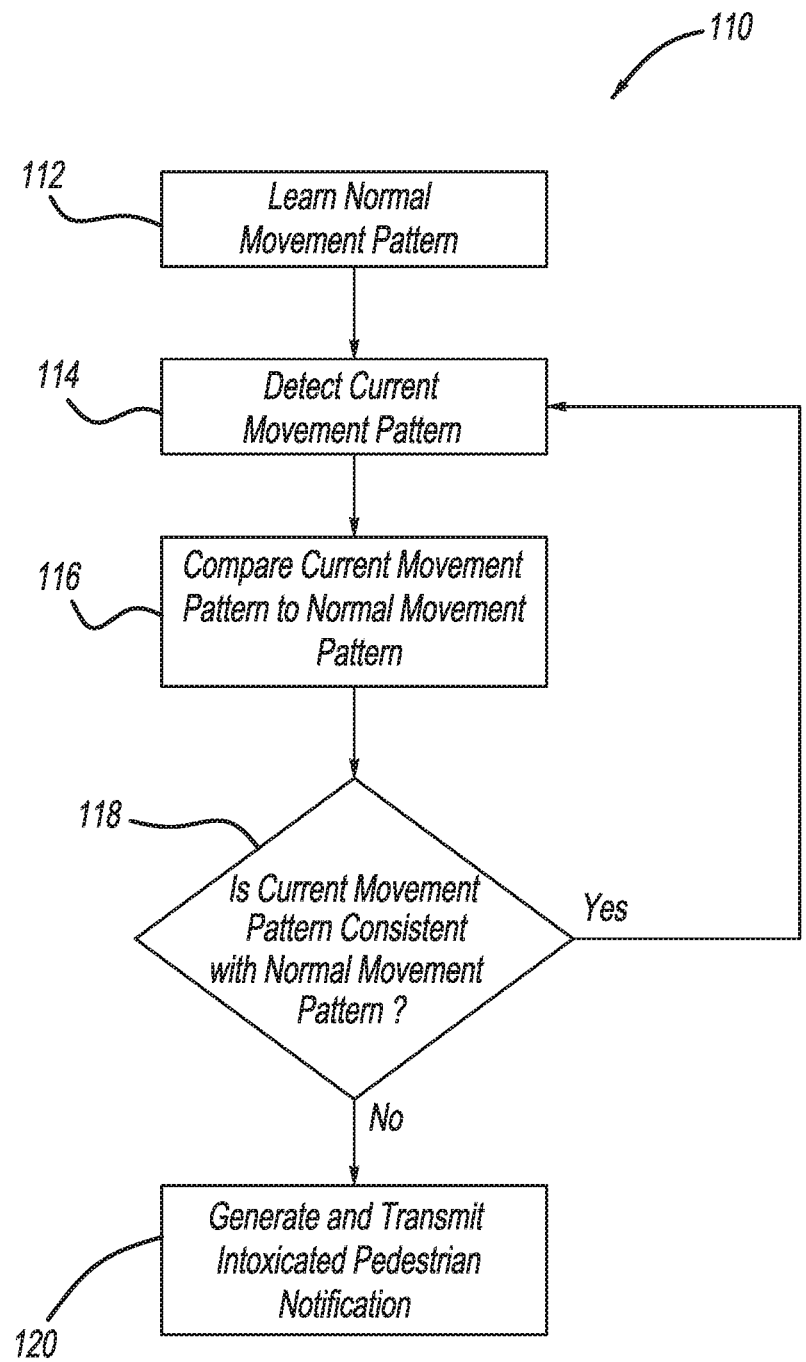
FIG. 3 is a method according to the present teachings for detecting an intoxicated pedestrian and notifying others nearby of the intoxicated pedestrian.

The components of the device 10 illustrated in FIG. 2 will now be described in further detail in conjunction with the method 110 of FIG. 3. The method 110 is configured to determine whether the pedestrian 12 is intoxicated. With initial reference to block 112, the control module 20 is configured to learn normal movement patterns of the pedestrian 12. For example, when the control module 20 is set in a learning mode, or at times when the pedestrian 12 is known to not be intoxicated, the control module 20 receives inputs from one or more of the movement detectors 32, 34, 36, and 38, analyzes movements of the pedestrian 12 over a predetermined period of time, and generates a movement pattern or profile, which the control module 20 saves in any suitable manner as a non-intoxicated (or sober) movement pattern for the pedestrian 12. After the control module 20 has "learned" the sober movement pattern of the pedestrian 12, the control module 20 is ready to monitor future movements of the pedestrian 12 to determine whether the pedestrian 12 is intoxicated.

Specifically and with reference to block 114, the control module 20 is configured to detect a current movement pattern of the pedestrian 12 based on inputs from one or more of the movement detectors 32, 34, 36, and 38 to determine whether the pedestrian 12 is intoxicated. After the current movement pattern of the pedestrian 12 has been detected and tracked for a predetermined period of time, at block 116 the control module 20 compares the current movement pattern of the pedestrian 12 to the stored normal movement pattern of the pedestrian 12 when the pedestrian 12 is sober. With reference to block 118, if the detected current movement pattern is consistent with the normal movement pattern of the pedestrian 12, the method 110 returns to block 114 where the control module 20 continues to detect the current movement pattern of the pedestrian 12. If at block 118 the control module 20 determines that the current movement pattern is not consistent with the normal (i.e., sober) movement pattern of the pedestrian 12, the control module 20 determines that the pedestrian 12 is intoxicated, and the method 110 proceeds to block 120.

At block 120, the control module 20 generates, and the transmitter 50 transmits, an intoxicated pedestrian notification. The intoxicated pedestrian notification is transmitted in any suitable manner, such as by any suitable radio frequency transmission protocol. For example, the intoxicated pedestrian notification can be transmitted by DSRC, any suitable Wi-Fi signal, any suitable LTE signal, etc. The transmitter 50 transmits the intoxicated pedestrian notification to any suitable receiver 60. The receiver 60 can be any suitable receiver configured to receive the intoxicated pedestrian notification transmitted by the transmitter 50.

For example, the receiver 60 can be provided on any suitable vehicle to notify the operator of the vehicle that the pedestrian 12 is intoxicated so that the operator of the vehicle can take action to avoid and/or assist the pedestrian 12. The receiver 60 can also be included in any suitable portable electronic device, such as a smartphone or wearable electronic device. Thus other pedestrians nearby the pedestrian 12 in possession of a device with the receiver 60 will also be informed that the pedestrian 12 is intoxicated so that they can take appropriate action to assist and/or avoid the pedestrian 12. Law enforcement personnel may also be provided with devices including the receiver 60, thereby allowing them to tend to the intoxicated pedestrian 12 as appropriate.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A device configured to detect when a pedestrian is intoxicated, the device comprising:
    at least one movement detector configured to detect a movement pattern of the pedestrian;
    a control module configured to compare the detected movement pattern of the pedestrian with a normal movement pattern of the pedestrian; and
    a transmitter configured to transmit a notification to drivers informing drivers that the pedestrian is intoxicated when the detected movement pattern does not correspond to the normal movement pattern;
    wherein when the pedestrian is known to not be intoxicated, the control module is configured in a learning mode in which the control module analyzes movements of the pedestrian over a predetermined period of time based on inputs from the at least one movement detector, generates the normal movement pattern based on the movements, and stores the normal movement pattern.

2. The device of claim 1, wherein the device is any one of a mobile smartphone and a wearable device.

3. The device of claim 1, wherein the at least one movement detector includes at least one of the following: an accelerometer; a compass; a GPS module; a GNSS module; and a gyroscope.

4. The device of claim 1, wherein the transmitter is a dedicated short range communication (DSRC) transmitter.

5. The device of claim 1, wherein the transmitter includes at least one of a WiFi transmitter and a cellular transmitter.

6. The device of claim 1, wherein the control module is configured to store the normal movement pattern.

7. The device of claim 1, wherein the transmitter is configured to transmit the notification to electronic devices of other pedestrians.

8. A system configured to detect when a pedestrian is intoxicated, the system comprising:
    a portable device configured to be transported with the pedestrian, the portable device including:
        at least one movement detector configured to detect a movement pattern of the pedestrian;
        a control module configured to compare the detected movement pattern of the pedestrian with a normal movement pattern of the pedestrian;
        a transmitter configured to transmit a notification that the pedestrian is intoxicated when the detected movement pattern is different from the normal movement pattern; and
    a receiver included with a secondary device, the receiver configured to receive the notification indicating that the intoxicated pedestrian is nearby;
    wherein when the pedestrian is known to not be intoxicated, the control module is configured in a learning mode in which the control module analyzes movements of the pedestrian over a predetermined period of time based on inputs from the at least one movement detector, generates the normal movement pattern based on the movements, and stores the normal movement pattern.

9. The system of claim 8, wherein the portable device is any one of a mobile smartphone and a wearable device.

10. The system of claim 8, wherein the at least one movement detector includes at least one of the following: an accelerometer; a compass; a GPS module; a GNSS module; and a gyroscope.

11. The system of claim 8, wherein the transmitter and the receiver are each configured for dedicated short range communication (DSRC).

12. The system of claim 8, wherein the transmitter includes at least one of a WiFi transmitter and a cellular transmitter.

13. The system of claim 8, wherein the control module is configured to store the normal movement pattern.

14. The system of claim 8, wherein the secondary device is a vehicle or a wearable device.

15. A method for detecting whether a pedestrian is intoxicated, the method comprising:
    detecting a current movement pattern of the pedestrian with a movement detector of a portable device in the pedestrian's possession;
    comparing, with a control module of the portable device, the detected movement pattern with a normal movement pattern of the pedestrian;
    transmitting an intoxicated pedestrian notification from the portable device when the detected movement pattern is different from the normal movement pattern; and
    when the pedestrian is known to not be intoxicated, the control module analyzes movements of the pedestrian over a predetermined period of time based on inputs from the movement detector, generates the normal movement pattern based on the movements, and stores the normal movement pattern.

16. The method of claim 15, wherein the portable device is any one of a mobile smartphone or a wearable smart device.

17. The method of claim 15, further comprising detecting the current movement pattern with at least one of an accelerometer, a compass, a GPS module, a GNSS module, and a gyroscope.

18. The method of claim 15, further comprising transmitting the intoxicated pedestrian notification to a receiver of a secondary device, the secondary device is a vehicle or a wearable device.

19. The method of claim 15, further comprising transmitting the notification by at least one of dedicated short range communication (DSRC), WiFi transmission, and cellular transmission.

20. The method of claim 15, wherein the normal movement pattern is stored in the portable device.

\* \* \* \* \*